(12) United States Patent
Cornish et al.

(10) Patent No.: US 6,854,344 B2
(45) Date of Patent: Feb. 15, 2005

(54) SAMPLE RETRIEVAL DEVICE FOR AEROSOL COLLECTION

(75) Inventors: Timothy J. Cornish, Catonsville, MD (US); Frederick P. Gick, Woodbine, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/728,297

(22) Filed: Dec. 4, 2003

(65) Prior Publication Data

US 2004/0118222 A1 Jun. 24, 2004

Related U.S. Application Data

(60) Provisional application No. 60/434,614, filed on Dec. 19, 2002.

(51) Int. Cl.[7] ................................................. G01N 1/00
(52) U.S. Cl. ................................. 73/863.22; 74/864.31
(58) Field of Search ............................ 73/28.01, 28.02, 73/28.04, 28.05, 28.06, 863.22, 863.23, 863.31, 863.33, 864.31, 864.81, 864.33, 864.34, 864.73

(56) References Cited

U.S. PATENT DOCUMENTS

| 3,802,167 | A | | 4/1974 | Turman |
| 4,226,115 | A | * | 10/1980 | Williams et al. ........... 73/28.04 |
| 4,321,822 | A | | 3/1982 | Marple et al. |
| 4,391,151 | A | | 7/1983 | Nelson et al. |
| 4,640,140 | A | * | 2/1987 | Burghoffer et al. ...... 73/863.22 |
| 4,795,612 | A | | 1/1989 | Keller |
| 5,201,231 | A | * | 4/1993 | Smith ...................... 73/863.22 |
| 5,722,618 | A | * | 3/1998 | Jacobs et al. ............. 244/137.1 |
| 5,874,046 | A | * | 2/1999 | Megerle ..................... 422/68.1 |
| 6,010,554 | A | * | 1/2000 | Birmingham et al. .......... 95/32 |
| 6,409,198 | B1 | * | 6/2002 | Weimer et al. ......... 250/339.04 |
| 6,463,814 | B1 | * | 10/2002 | Letarte et al. ........... 73/863.22 |
| 2002/0124664 | A1 | | 9/2002 | Call et al. |

FOREIGN PATENT DOCUMENTS

JP          55-116416          9/1980

* cited by examiner

*Primary Examiner*—Robert Raevis
(74) *Attorney, Agent, or Firm*—Albert J. Fasulo, II

(57) ABSTRACT

A modular aerosol sample detection system is provided comprising a sample collector couplable to an aerial vehicle and provided with at least one retrievable collection sample plate, which controllably rotates to collect aerosol samples on a multiplicity of collection spots arranged in multiple concentric tracks on the collection disk, and a multi-channel TOF removably couplable to the collection sampler to analyze the collected samples.

26 Claims, 2 Drawing Sheets

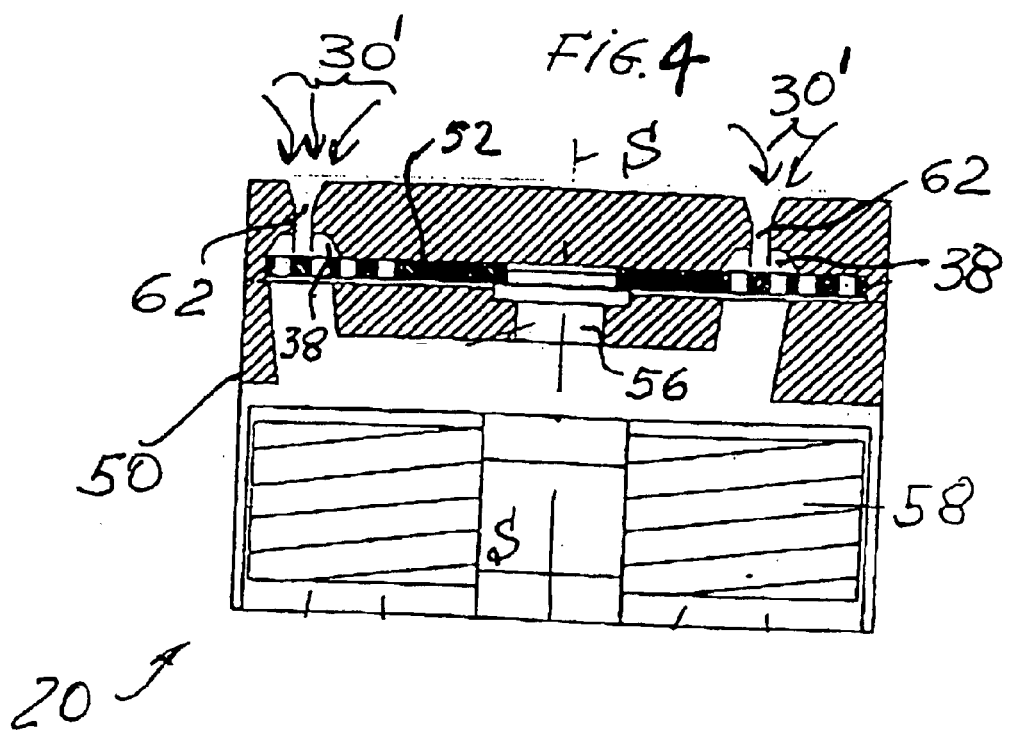
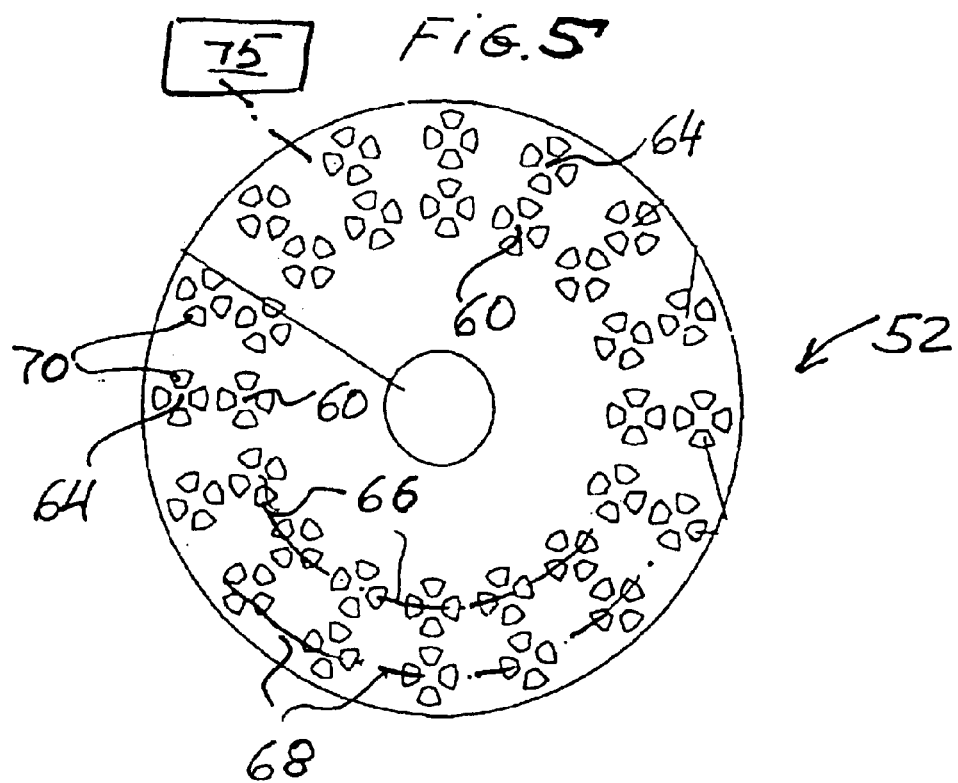

SAMPLE RETRIEVAL DEVICE FOR AEROSOL COLLECTION

CROSS REFERENCE TO RELATED APPLICATIONS

This application claims the benefit of prior filed U.S. Provisional Application No. 60/434,614, filed on Dec. 19, 2002, the contents of which are incorporated by reference herein.

BACKGROUND OF THE INVENTION

1. Field of the Invention

The present invention generally relates to a sample retrieval device for aerosol collection.

2. Discussion of the Related Art

Aerosol sampling has become an indispensable process used in a wide range of applications such as, for example, environmental studies, detection of airborne biological or chemical warfare agents, exploration of cosmos, etc. The collection of the impurities, especially in air, can be realized by filtering many particles out of the air. The detection of the collected particles can be performed by, among others, sophisticated diagnosing equipment, e.g., time-of-flight spectrometers.

Recently, aerosol sample retrieval for chemical analysis by mass spectrometry has developed into an alternative method to on-site monitoring by separating a collection device from an analytical instrumentation. As a consequence, the use of aerosol collecting devices has been diversified and expanded to areas previously considered to be hardly accessible.

Some of the known collecting devices operate as an impacting type device configured to force entrained particles along a path, which leads the particles to an impactor plate, where these particles are collected upon impact and later analyzed. One of the difficulties in using impactors can be explained by a high kinetic energy possessed by particles entrained in a gas stream. As a consequence, the entrained particles can bounce off the impactor plate and re-entrain the gas stream thereby causing erroneous results during a subsequent analysis. Another difficulty includes a non-uniform deposit over the entire impaction plate, which is ordinarily mounted stationary mounted relative to a particle guide. However, it is desirable that a deposit be substantially uniform, because it reduces particle re-entrainment.

To remedy these problems, a "virtual" impactor has been developed to separate particulates from a fluid stream with techniques other than direct impaction. Virtual impactors may operate on a number of different principles, but all avoid actual "impact" as a means to separate particulates from a fluid in which the particulates are entrained. Critically, virtual impactors invariably rely on differences in particulate mass to induce inertial separation.

Still, the problems associated with actual impactors continue to persist in virtual impactors known for particle "wall loss," i.e., unintended deposition of particulates on various surfaces of virtual impactor structures, especially at curved or bent portions. As a consequence, the virtual impactors are characterized complicated configurations, time-consuming installation and cost inefficient maintenance.

Thus, many of the known types of the actual and virtual impactors are characterized by a rather expensive and delicate structure difficult to install and maintain.

It would therefore be desirable to provide a cost-efficient, maintenance-friendly and rugged aerosol collection device, which can be coupled to a vehicle to collect aerosol samples in inaccessible or hazardous environment in a reliable manner.

SUMMARY OF THE INVENTION

In one embodiment of the present invention, a sample collector is provided and is at least configured to be removably coupled to a vehicle and having multiple intake ports and a rotary collection plate, which are juxtaposed with one another to provide a plurality of concentric tracks of collection spots on the sampling surface to allow for redundancy in the sample collection.

The sample collector of the present invention has been found to be particularly advantageous when formed from lightweight materials and used with Unmanned Aerial Vehicles (UAV), e.g., radio controlled electric powered helicopter (RC UAV), which allows for high versatility, maneuverability, and rapid interrogation of otherwise inaccessible and/or hazardous environments. Other advantages of the UAV are its broad commercial availability, relatively cost-efficient and simple structure capable of carrying a payload of up to a pound. As one skilled in the art would readily appreciate, although the following discussion is directed to RC UAV's, the sample collector of the present invention can be associated with any type of vehicle subject only to elementary mechanical modifications of the mounting structure of the device.

In accordance with another aspect of the present invention, a sample collector is centered along an axis of symmetry and configured so that an air sample, traversing multiple intake ports, is branched among multiple outlet ports positioned asymmetrically relative to the axis of symmetry. The geometry of the intake and outlet ports, each pair of which defines a respective air passage therebetween, can vary subject only to the formation of the multiple tracks of collection points on the rotary plate.

In accordance with a further aspect of the present invention, the sampling surface is configured as a disk formed with a multiplicity of concentric arrays of ventilation holes. Each array is divided into numerous groups each including several ventilation holes, which surround a respective continuous region of the disk to define a collection point. Hole size affects a filtering capacity of the disk and can vary in accordance with a given task and local requirements.

It is important to note that the manner in which samples are collected affects the usefulness of the samples for archival purposes. Collected samples are often employed to determine more information about an event occurring at a specific time. For example, archival data collected during a predetermined time and itinerary of flight might be used to determine at what time higher levels of pollution occurred. That time could then be applied to determine at which point of the itinerary such a peak was detected to undertake further necessary measures depending on the determined locale and level of detected pollutants or agents.

This feature can be addressed in accordance with a further aspect of the present invention by providing a method and device capable of collecting samples for successive sampling periods, and which include time indexing enabling a specific collected sample to be correlated with a specific time at which the sample was taken.

In accordance with another aspect of the invention, a sample collector is an integral part of a collector/analyzer assembly configured in accordance with the present invention. In this manner, not only can the sample collector possess the increased collecting capability, but also it can be readily coupled to a multi-channel time of flight (TOF) mass analyzer to provide for a time-efficient, reliable process.

The sample collector of the present invention provides for a simple and cost efficient structure configured to provide numerous sample collections and sample identifications while being mounted to a variety of vehicles operating in hazardous environments.

BRIEF DESCRIPTION OF THE DRAWINGS

The above and other features and advantages will become more readily apparent from the detailed description of the invention accompanied by the following drawings, in which:

FIG. 4 is a cutaway side view of the sample retrieval device of the present invention; and, FIG. 5 is a plan view of a sample disk configured in accordance with the present invention.

DETAILED DESCRIPTION OF THE PREFERRED EMBODIMENTS

Figure 1:
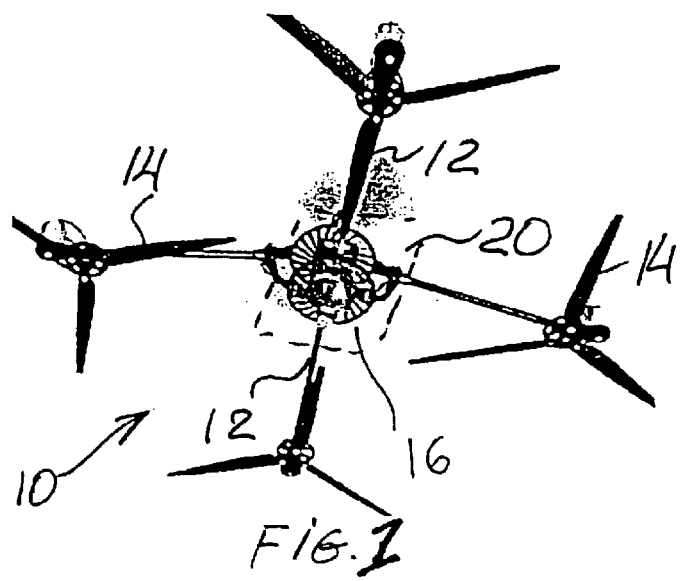
FIG. 1 is a view illustrating the sample retrieval collection device mounted to a radio-controlled unmanned aerial vehicle of the present invention.
Figure 2:
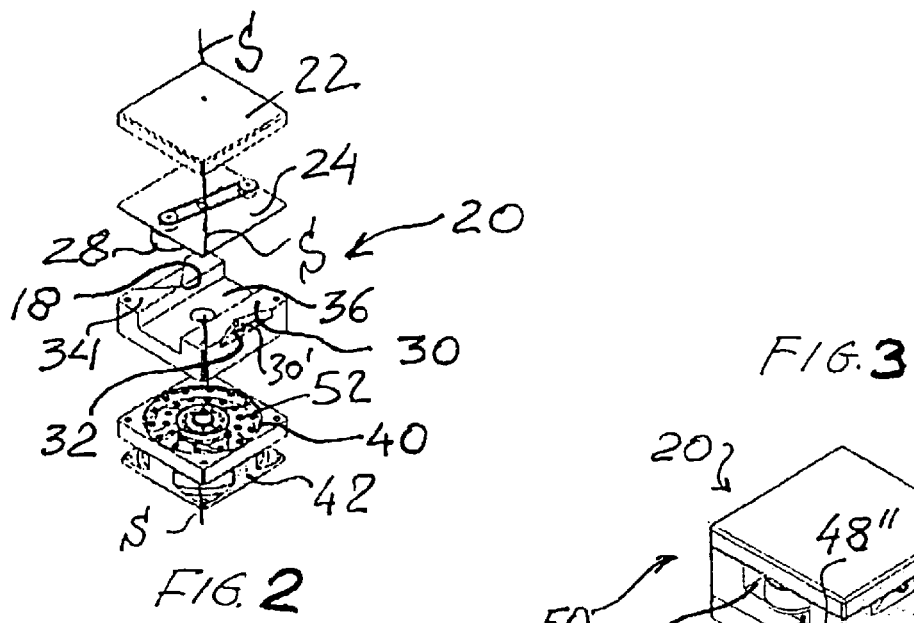
FIG. 2 is an exploded view of the sample retrieval device of the present invention.
Figure 3:
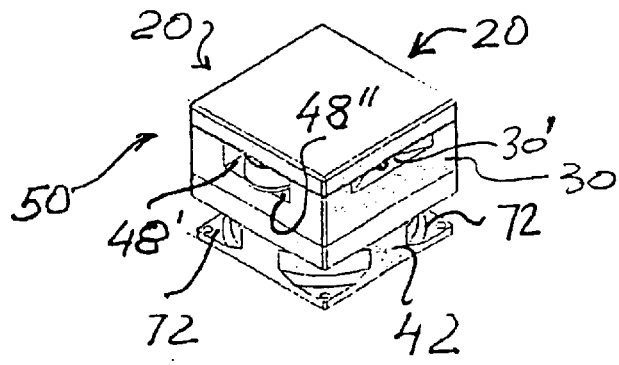
FIG. 3 is an isometric view of the sample retrieval device of the present invention.

Referring to FIG. 1-4, sample retrieval device 20 is configured to at least perform numerous collections of aerosol samples in remote and hazardous areas reachable by man or remote operated vehicles. Particularly well suited as a carrier for the device 20 is a radio controlled (RC) battery operated helicopter 10 or an RC Unmanned Aerial Vehicle (RC UAV) 10, as illustrated in FIG. 1. Both highly maneuverable and easily assembleable, the RC UAV has a lightweight carbon fiber body including multiple arms 12, each of which has a rotor blade assembly 14 powered by a battery set. A central control module 16 including electronics is mounted on the vehicle's body equidistantly from the rotary blade assemblies 14 and can be configured to carry the device 20, preferably attached to the bottom of the control module. Compared to liquid operated helicopters, the RC UAV is particularly advantageous for collecting air samples, because the latter are not compromised by otherwise contaminating fuels.

Turning specifically to FIGS. 2–4, the device 20 can be powered by its own power source, with the batteries of the RC UAV 10 being preferred, and is characterized by a housing 50 having any suitable shape, e.g., a polygonal shape or a circular shape. In either case, the device 20 is highly portable and designed, for example, to be about 3" long and wide and about 3" high.

Housing 50 of device 20 is configured to contain one or more sample plates 52 each optionally having a disk shape, such as, for example, a standard about 3" diameter disk mounted on a base 42 of the device. To reliably mount the disk 52, the base 42 has an aperture 40 dimensioned to fully receive the disk 52, which is thus reliably secured in the housing. Housed in base 42 is a motor 56 (FIG. 4) coupled to and rotating the disk 52 which receives and collects a plurality of air samples during the flight of the helicopter, as will be explained below.

To prevent interference of device 20 with the aerial maneuverability of the RC UAV 10, housing 50 is configured with air passages 48' and 48" (FIG. 3) located between base 42 and top 22 of housing 50 and extending through the housing to substantially reduce the air resistance of the device during a flight. Formation of air passages 48' and 48" can be obtained by an air-intake housing part 30 (FIG. 2), juxtaposed with base 42, and lid 24 coupled to the upper portion of the air-intake part 30. In particular, the air-intake part 30 is shaped to have a flat lower portion totally covering the aperture 40 and a recessed upper portion configured to have a pair of side flanges 34 extending from a bottom 36. The lower portion of the lid 24 carries one or more spacers 28 (FIG. 3) supported by bottom 36 and dimensioned to form the air passages 48' and 48", each of which is defined between the spacer(s) and a respective one of the flanges 34. The spacer(s) 28 may be variously shaped and dimensioned and is subject only to the dimensional limitations necessary to provide air passages. Coupling top 22, lid 24, air-intake part 30 and base 42 to one another can be realized by a plurality of fasteners (not shown) preferably extending through the corners of the of device 20.

To provide flow of air through device 20, base 42 can house a fan 58 (FIG. 4) located under motor 56 and disk 52 and operative to create a negative pressure, which is sufficient to force ambient air through multiple intake ports 30'. The intake ports are provided in cutout regions 32 each formed in a respective one of the flanges 34 of the air-intake part 30 (FIG. 2) of the housing 50. The configuration of the intake ports guides air samples through a plurality of passages 62 leading towards disk 52, which is positioned to be impacted by the air streams and configured to allow numerous collections during a flight.

The disk(s) 52, rotatable relative to the passages 62, are advantageously fabricated so that two tracks of collections spots 60 and 64 are arranged in concentric inner 66 and outer 68 circular tracks, respectively, as shown in FIG. 5. Arrangement of multiple concentric tracks of collection spots 60, 64 is determined by the configuration of and position of each of the downstream ends or outlets 38 (FIG. 4) of the passages 62 relative to an axis of symmetry S—S (FIG. 4) of the device 20. Forming the downstream ends asymmetrically relative to the axis S—S allows for as many concentric arrays as the number of intake passages, which may be more than two depending on the arrangement of the cutout regions 32. Since the increased volume of the sample is desirable, the outlet ports 38 are dimensioned to be larger than the rest of the passages.

Preferably, the cutout regions 32 each have a triangular cross-section provided with an apex 18 (FIG. 2), which is located next to a respective intake port 30' (FIGS. 3 and 4), and serve as an airflow trap of air forced into these ports. Since the air passages are formed parallel, the apexes 18 are located asymmetrically to the axis S-S to form two concentric arrays of collections spots as shown in FIG. 2. However the parallel relationship between the passages is not critical; it is the downstream ends of these passages that define a multi-track collection spot arrangement on the disk 52. As a consequence, the cutout regions can be uniform, and the intake ports can be spaced symmetrically from the axis of symmetry S—S, provided that the air passages extend angularly towards one another to have their downstream ends terminate asymmetrically relative to this axis. Alternatively, a micro-porous material (frit or filter) may be used for the collection surface for trapping particulates entrained in the air stream.

The motor 56 can be, for example, a stepping motor rotatably fixed to the disk 52, which is thus indexed so that any given pair of spaced across the sample disk 52 collection spots 60 and 64 of the inner 66 and outer 68 tracks, respectively, is always aligned with the outlet ports 38. As a consequence, the multiples concentric tracks of collection spots allow for redundancy in the sample, which, in turn, provides for more reliable detection of the collected samples.

While the sampling surface of the disk 52 is prepared using, for example, activated charcoal, adhesives, or other sample captivating substances, areas surrounding each of the collection spots 60 and 64 each are drilled with an array of vent holes 70 (FIG. 5) traversed by passing air flow. The shape, dimension and quantity of the vent holes can be selected to address the local requirements. To evacuate the air from the housing 50, base 42 (FIG. 3) is provided with numerous recesses 72 providing flow communications between the interior of the housing and the atmosphere.

Following the collection cycle, helicopter 10 is recovered, the sample disk 52 is removed, and subsequently loaded into a multi-channel time of flight (TOF) mass analyzer 75 (FIG. 5), e.g., a multi-channel time of flight (TOF) mass analyzer as disclosed in U.S. Pat. No. 6,580,070 to Cornish et al., the contents of which are incorporated by reference herein. The multiple tracks are indexed through the multiple mass spectrometer channels allowing for a rapid and redundant assessment of the environmental aerosol sample.

It will be understood that various modifications may be made to the embodiments disclosed herein. Therefore, the above description should not be construed as limiting the scope of the invention, but merely as exemplifications of the preferred embodiments. Those skilled in the art will envision other modifications within the scope and spirit of the claims appended hereto.

What is claimed is:

1. An aerosol sample detection system comprising:
 a sample collector removably attachable to a vehicle and comprising:
  a housing having an interior;
  a plurality of passages formed in the housing and configured to simultaneously provide multiple flows of aerosol sample into the interior thereof from ambient; and,
  a sample plate removably mounted in the interior of the housing downstream of the plurality of passages and having a sample surface, which is juxtaposed with the plurality of passages, the sample plate and the plurality of passages being displaceable relative to one another so that multiple concentric tracks of collection spots of the aerosol sample are formed on the sample surface upon impacting the multiple flows of the aerosol sample thereagainst; and
 a multi-channel time of flight (TOF) mass analyzer provided with multiple channels and configured to receive the sample plate, wherein when the sample plate is removed from the sample collector and loaded into the mass analyzer, the multiple concentric tracks on the sample surface each are indexed through a respective one of multiple channels of the TOF mass analyzer.

2. The aerosol sample detection system of claim 1, further comprising a pressure source mounted in the housing downstream from the sample plate and including a fan or a pump to provide pressure differential between the interior of the housing and the ambient, which is sufficient to force air along the plurality of passages into the interior of the housing.

3. The aerosol sample detection system of claim 2, wherein the housing has a modular configuration extending along a symmetry axis and including a base configured to house the pressure source spaced axially downstream of the sample plate, an intermediary air intake part of the housing provided with the plurality of passages and covering the sample surface, and a cover topping the intermediary air intake part, wherein the base, the intermediary air intake part and the cover coextend with one another in a plane perpendicular to the symmetry axis and are detachably coupled to one another.

4. The aerosol sample detection system of claim 3, wherein the base of the housing is provided with multiple air outlets and has a recessed surface shaped and dimensioned to receive the sample plate.

5. The aerosol sample detection system of claim 4, wherein the intermediary air intake part of the housing has a lower flat surface covering the recessed surface of the base and an upper surface having a flat bottom spaced from the lower flat surface and a pair of flanges spaced across the flat bottom and extending axially upwards therefrom.

6. The aerosol sample detection system of claim 5, wherein the cover abuts the pair of flanges and is provided with at least one spacer extending axially toward and pressing against the flat bottom, the at least one spacer being dimensioned to form a pair of air channels defined between the at least one spacer and a respective one of the pair of flanges.

7. The aerosol sample detection system of claim 5, wherein the pair of flanges each have a respective cutout region extending laterally inwards toward the cutout region of the other flange and traversed by a respective one of the plurality of passages leading into the recessed surface of the base and terminating upstream of the sample surface of the sample plate.

8. The aerosol sample detection system of claim 7, wherein the cutout regions each have a respective substantially triangular shape and is provided with a respective apex spaced from the symmetry axis and located next to an intake port, which is formed in each of the cutout regions and is in flow communication with a respective one of the plurality of the passages traversed by the aerosol sample.

9. The aerosol sample detection system of claim 8, wherein the cutout regions are non-uniformly dimensioned to have the apexes thereof spaced asymmetrically relative to the symmetry axis.

10. The aerosol sample detection system of claim 1, further comprising a drive mounted in the housing and removably coupled to the sample plate rotatable so that the plurality of passages each have a respective downstream outlet port facing the sample surface and controllably juxtaposed with the collection spots of the multiple concentric tracks.

11. The aerosol sample detection system of claim 10, wherein the drive is a stepper motor coupled to the sample plate.

12. The aerosol sample detection system of claim 11, wherein the sample plate is disk-shaped and is rotatably fixed to a shaft of the stepper motor.

13. The aerosol sample detection system of claim 11, wherein the sample surface is indexed through the collection spots of the concentric tracks by the stepper motor to allow numerous collections of the aerosol sample to be performed during displacement of the sample plate and the plurality of passages relative to one another.

14. The aerosol sample detection system of claim 10, wherein the sample plate has a plurality of groups of spaced apart ventilation holes, each group of ventilation holes being arranged to surround a respective one of the collection spots of each of the concentric tracks on the sample surface of the sample plate.

15. The aerosol sample detection system of claim 1, wherein the sample surface includes a substrate selected from the group consisting of charcoal or adhesives.

16. The aerosol sample detection system of claim 1, wherein the plurality of passages extend substantially parallel to one another and are spaced asymmetrically relative to a symmetry axis of the housing to provide parallel multiple flows of aerosol sample through the housing.

17. The aerosol sample detection system of claim 1, wherein the sample surface is made from a micro-porous material including flit or filter configured to trap particulates entrained in the aerosol sample.

18. An aerosol sample detection system comprising:
 a radio controlled unmanned aerial vehicle (RC UAV) having:
  a plurality of rotary blades each powered by a battery set; and
  a control panel spaced equidistantly from the plurality of rotary blades; and,
 an aerosol collector removably mounted to the control panel and operative to collect multiple aerosol samples, the aerosol collector comprising:

a housing having an interior and an axis of symmetry;

a plurality of passages formed in the housing and spaced asymmetrically with respect to the axis of symmetry;

a sample plate rotatable about the axis of symmetry and removably mounted in the interior of the housing downstream of the plurality of passages, the sample plate having a sample surface juxtaposed with the plurality of passages;

a fan, mounted in the housing downstream from the sample plate, that draws multiple flows of aerosol sample from ambient through the plurality of asymmetric passages and toward the sample surface; and a stepper motor mounted in the housing and configured to rotate the sample surface about the axis of symmetry such that the multiple flows of aerosol sample impact the sample surface as it rotates so as to form multiple separated concentric circular tracks of collection spots thereon, the circular concentric tracks having (i) their respective centers coinciding with the axis of symmetry, and (ii) different respective radii.

19. The aerosol detection system of claim 18, further comprising a time of flight (TOF) mass analyzer configured to receive the sample plate and provided with multiple channels, wherein when the sample plate is removed from the sample collector and loaded into the mass analyzer, the multiple concentric tracks formed on the sample surface of the sample plate each are indexed through a respective one of the multiple channels of the TOF mass analyzer.

20. A method of detecting an aerosol sample comprising the steps of:

mounting an aerosol collector to a radio-controlled unmanned aerial vehicle, said mounting step comprising the further steps of:

providing a housing centered along a symmetry axis;

providing a plurality of passages extending through the housing and configured to simultaneously guide multiple flows of the aerosol sample through the housings and asymmetrically with respect to the symmetry axis;

removably placing a sample plate within the housing so that a sample surface of the sample plate opposes downstream ends of the plurality of passages; and, rotating the disk during a flight of the aerial vehicle about the symmetry axis and relative to the plurality of passages; and creating a negative pressure within the aerosol collector, wherein said negative pressure causes the multiple flows of the aerosol sample to impact the rotating sample surface so as to form multiple separated concentric circular tracks of collection spots thereon, the circular concentric tracks having (i) their respective centers coinciding with the symmetry axis, and (ii) different respective radii.

21. The method of claim 20, further comprising the steps of:

removing the sample plate from the housing; and, loading the sample plate into a time of flight (TOF) mass analyzer provided with multiple channels, wherein the multiple concentric tracks each are indexed through a respective one of the multiple channels of the TOF mass analyzer.

22. The method of claim 21, wherein the step of loading comprises the step of redundantly assessing the aerosol sample collected on a group of spaced across the sample plate collection spots of the multiple concentric tracks.

23. The method of claim 20, wherein the step of rotating is provided in a time- and speed-controlled manner, thereby indexing each collection spot of the multiple concentric tracks, the method further comprising the step of continuously powering the sample collector during a flight of the radio-controlled unmanned aerial vehicle.

24. An aerosol collector comprising:

a housing having an interior and an axis of symmetry;

a plurality of passages formed in the housing and spaced asymmetrically with respect to the axis of symmetry;

a sample plate rotatable about the axis of symmetry and removably mounted in the interior of the housing downstream of the plurality of passages, the sample plate having a sample surface juxtaposed with the plurality of passages;

a fan, mounted in the housing downstream from the sample plate, that draws multiple flows of aerosol sample from ambient through the plurality of asymmetric passages and toward the sample surface; and a stepper motor mounted in the housing and configured to rotate the sample surface about the axis of symmetry such that the multiple flows of aerosol sample impact the sample surface as it rotates so as to form multiple separated concentric circular tracks of collection spots thereon, the circular concentric tracks having (i) their respective centers coinciding with the axis of symmetry, and (ii) different respective radii.

25. The aerosol sample detection system of claim 10, wherein the collection spots of each of the multiple concentric tracks are spaced uniformly from one another at a respective angular distance, the uniform angular distance between the collections spots of one of the multiple concentric tracks being different from the uniform angular distance between the collection spots of another one of the multiple concentric tracks.

26. The aerosol sample detection system of claim 10, wherein the collection spots of the multiple concentric tracks are arranged to have each of the collection spots of one of the multiple concentric tracks aligned with and spaced across the sample plate from a respective collection spot of another one of the concentric tracks, wherein the aligned and spaced apart collections spots of the concentric tracks are impinged simultaneously by the multiple flows of aerosol sample exiting the outlet ports of the plurality of passages to allow for redundancy in collection of the aerosol sample on the sample surface of the sample plate.

* * * * *